United States Patent
Chen et al.

(10) Patent No.: US 10,557,962 B2
(45) Date of Patent: Feb. 11, 2020

(54) METHOD FOR MEASUREMENT OF HYDROCARBON CONTENT OF TIGHT GAS RESERVOIRS

(71) Applicant: Saudi Arabian Oil Company, Dhahran (SA)

(72) Inventors: Jinhong Chen, Katy, TX (US); Stacey M. Althaus, Houston, TX (US); Daniel T. Georgi, Houston, TX (US); Hui-Hai Liu, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 122 days.

(21) Appl. No.: 15/268,022

(22) Filed: Sep. 16, 2016

(65) Prior Publication Data
US 2018/0081077 A1    Mar. 22, 2018

(51) Int. Cl.
*G01V 3/32* (2006.01)
*E21B 49/00* (2006.01)
*E21B 49/02* (2006.01)
*E21B 49/08* (2006.01)

(52) U.S. Cl.
CPC .............. *G01V 3/32* (2013.01); *E21B 49/00* (2013.01); *E21B 49/02* (2013.01); *E21B 49/08* (2013.01)

(58) Field of Classification Search
None
See application file for complete search history.

(56) References Cited

U.S. PATENT DOCUMENTS

| 3,409,092 A | 11/1968 | Doremus |
| 3,494,188 A | 2/1970 | Boatman |
| 6,453,727 B1 | 9/2002 | Lenormand et al. |

(Continued)

FOREIGN PATENT DOCUMENTS

WO   2011133859 A1   10/2011

OTHER PUBLICATIONS

Sigal Richard, NMR quantification of the gas resource in shale gas reservoirs; Oct. 27, 2011; The Boards of regents of the University of Oklahoma; Publication No. WO2011/133859 A1; G01V3/00.*

(Continued)

*Primary Examiner* — Nasima Monsur
(74) *Attorney, Agent, or Firm* — Bracewell LLP; Constance G. Rhebergen; Albert B. Kimball, Jr.

(57) ABSTRACT

Nuclear magnetic resonance (NMR) well logs are obtained from a well in the reservoir measures of the total fluid, including both water and hydrocarbon, in the shale of the reservoir. NMR measurement at the surface of shale subsurface samples obtained in from drill cuttings or core samples of the same well provide measures of total water content of the shale. At the surface, pressure on the subsurface sample becomes that of atmospheric pressure, and hydrocarbon gas contained in the shale cuttings bleeds off. The remaining fluid within the shale cuttings is then only water, which can be measured using NMR techniques. Compensation for the effect of drilling fluids (drilling mud) on the NMR measures from the fluid cuttings is also performed. The hydrocarbon gas content of the formation shale can be determined from the difference between formation NMR well log readings and NMR measurements from subsurface sample.

5 Claims, 5 Drawing Sheets

(56) References Cited

U.S. PATENT DOCUMENTS

| | | |
|---|---|---|
| 6,765,380 B2 | 7/2004 | Freedman |
| 6,958,604 B2 | 10/2005 | An et al. |
| 7,082,812 B2 | 8/2006 | Lenormand et al. |
| 7,131,317 B2 | 11/2006 | Lenormand et al. |
| 7,388,373 B2 | 6/2008 | Lenormand et al. |
| 7,924,001 B2 | 4/2011 | Minh |
| 8,686,724 B2 | 4/2014 | Mitchell et al. |
| 8,727,145 B2 | 5/2014 | Zollondz et al. |
| 8,857,243 B2 | 10/2014 | Valenza, II et al. |
| 8,967,249 B2 | 3/2015 | Akkurt et al. |
| 9,176,251 B2 | 11/2015 | Singer et al. |
| 2003/0094946 A1 | 5/2003 | Galford et al. |
| 2006/0272812 A1 | 12/2006 | Yu et al. |
| 2010/0127701 A1* | 5/2010 | Wichers ............... G01V 11/00 324/303 |
| 2012/0065890 A1* | 3/2012 | Liu ........................ E21B 49/00 702/13 |
| 2013/0113480 A1* | 5/2013 | Kadayam Viswanathan ............... G01V 3/32 324/303 |
| 2013/0234703 A1 | 9/2013 | Chen et al. |
| 2013/0282288 A1 | 10/2013 | Quinn et al. |
| 2014/0107928 A1* | 4/2014 | Roy ........................ G01V 3/32 702/7 |
| 2015/0219782 A1 | 8/2015 | Kadayam Viswanathan et al. |
| 2015/0240633 A1 | 8/2015 | Akkurt et al. |
| 2016/0061803 A1 | 3/2016 | Hadj-Sassi et al. |

OTHER PUBLICATIONS

Research Report—HRC-RET-201509-0xx; Method for Measurement of Hydrocarbon Content in Shale Gas Reservoir; Jinhong Chen, Stacey M. Althaus, and Hui-Hai Liu.

International Search Report and Written Opinion dated Oct. 26, 2017 for corresponding PCT/US2017/051527.

Boatman, W. A., "Measuring and Using Shale Density to Aid in Drilling W Measuring and Using Shale Density to Aid in Drilling Wells in High-pressure Areas"; American Petroleum Institute; 1967; API-67-121.

Lake, L., "Petroleum Engineering Handbook, vol. 6—Emerging and Peripheral Technologies", Society of Petroleum Engineers, Chapter 7, pp. 295-353.

Core Sample, Wikipedia, Oct. 2015, https://en.wikipedia.org/w/indexphy?title=Core_sample&oldid=686528528, pp. 1-6.

* cited by examiner

METHOD FOR MEASUREMENT OF HYDROCARBON CONTENT OF TIGHT GAS RESERVOIRS

BACKGROUND OF THE INVENTION

1. Field of the Invention

The present invention relates to evaluation of subsurface hydrocarbon reservoirs, and more particularly forming measures of the hydrocarbon content of tight gas reservoirs including shales, tight siliciclastic sands, and tight carbonates.

2. Description of the Related Art

In reservoir engineering, it has been important for reservoir evaluation to have as the starting point a measure of reserve or gas-in-place in a gas reservoir and volatile oil reservoir. However, for shale gas, so far as is known, no accurate method has been commonly accepted by the industry to estimate gas-in-place in a reservoir.

Existing methods have been based on above measures of water by laboratory testing of core samples obtained from cores extracted from subsurface formations by core sampling tools. There have been several deficiencies with existing methods. Obtaining cores with core sampling tools at depths of interest in a formation is expensive. Side-wall cores are thus generally only obtained at a few sporadic locations from a well. In addition once the cores have been obtained, their preservation to maintain fluid content for accurate results during ongoing laboratory evaluation and analysis of the reservoir has been notoriously difficult and full of uncertainty.

For unconventional shale gas reservoirs the presence of organic matter, in addition to the complex mineralogical composition, complicates the log based methods: the uncertainty in quantity and density of organic matter and other heavy minerals, such as pyrite, makes the density porosity inaccurate.

The large amount of hydrogen in organic matter and clay bound water leads to porosity estimation from neutron logs much higher than the real value. Resistivity logs fail to estimate water content in shale due to the presence of large amounts of clay and the associated surface conductivity. This excess conductivity must be accounted for. However, for clay rich shales, accounting for this excess conductivity can lead to large uncertainties in the computed water volumes.

For the core-measurement based methods, the basic porosity measurement in tight nanoporous shales is problematic. The extremely small dimensions of the pores make it difficult to clean and dry the pores. If the pores are not cleaned and dried, conventional porosity measurement methods do not provide accurate porosities. For example if the pores remain filled with water, it is not possible to expand helium into the pore space and quantitatively determine how much pore space there is in the sample.

Even when the porosity is accurately obtained, it remains difficult to estimate the hydrocarbon content based on porosity because a hydrocarbon storage model is required, which has not been reliably established. Shale contains three type of porosity, namely mineral-matrix porosity, organic-matter porosity, and fracture pores. It is not clear if hydrocarbon and/or water are present in all or only some of these pores in the reservoir. In addition, the adsorption on the pore surface can contribute a significant amount of reserve in a nanoporous system. However, the amount of adsorbed hydrocarbon at the reservoir condition may not be readily obtained from a laboratory measurement because all the pore surfaces, including those pores that only hold water in the reservoir, can contribute to the laboratory measurement. Furthermore, the presence of heavy hydrocarbons may result in capillary condensation in some shale gas reservoirs. In this condition, pore surface property and pore size distribution significantly impact the hydrocarbon in place. Therefore, laboratory measured porosity only has some guidance value in the estimation of hydrocarbon content for shale gas reservoir.

SUMMARY OF THE INVENTION

Briefly, the present invention provides a new and improved method of determining hydrocarbon gas content of a subsurface shale formation in the earth. Nuclear magnetic resonance well log measures are obtained from a well in the subsurface shale formation, and a measure of the total fluid content in situ of the subsurface shale formation is obtained from these nuclear magnetic resonance well log measures.

Samples of the subsurface shale formation are obtained, and nuclear magnetic resonance measures are obtained from the subsurface samples. A measure of the water content in the subsurface samples is obtained from the nuclear magnetic resonance measures from the subsurface samples in the presence of drilling mud. The hydrocarbon gas content of the shale formation is determined from the measure of the total fluid content in situ of the subsurface shale formation and measure of the water content in the formation samples.

The present invention also provides a new and improved computer implemented method of determining hydrocarbon gas content of a subsurface shale formation in the earth. A measure is formed of the fluid content in situ of the subsurface shale formation obtained by a nuclear magnetic resonance well log from a well in the subsurface shale formation. Measures are formed of the volume of total fluids present in samples of the well from the subsurface shale formation based on nuclear magnetic resonance spectra obtained from the samples.

Measures are formed of the volume of water present in the subsurface sample based on nuclear magnetic resonance spectra obtained from the samples, measures of the weight, and measures of the volume of the drill fluids in the samples. A measure of the water content in the samples is formed, and the hydrocarbon gas content of the shale formation is determined from the measure of the fluid content in situ of the subsurface shale formation and measure of the water content in the samples.

The present invention also provides a new and improved data processing system for determining hydrocarbon gas content of a subsurface shale formation in the earth based on nuclear magnetic resonance measures. The data processing system includes a computer memory, which stores, as inputs, nuclear magnetic resonance well log measures obtained from a well in the subsurface shale formation. The computer memory also stores as inputs a measure of the fluid content in situ of the subsurface shale formation obtained from the well in the subsurface shale formation, and measures of the water content in the samples.

The data processing system according to the present invention also includes a processor, which forms a measure of the fluid content in situ of the subsurface shale formation based on nuclear magnetic resonance well log measures obtained by a nuclear magnetic resonance well log from a well in the subsurface shale formation. The processor also forms measures of the volume of total fluids present in the samples from the subsurface shale formation based on nuclear magnetic resonance spectra obtained from nuclear magnetic resonance measures of the samples.

The processor forms measures of the volume of water present in drill cuttings of the subsurface sample based on nuclear magnetic resonance spectra obtained from nuclear magnetic resonance measures of the samples, measures of the weight, and measures of the volume of drill fluids in the samples. The processor then determines the hydrocarbon gas content of the shale formation from the measure of the fluid content in situ of the subsurface shale formation and measure of the water content in the samples.

DETAILED DESCRIPTION OF THE PREFERRED EMBODIMENTS

Figure 1:
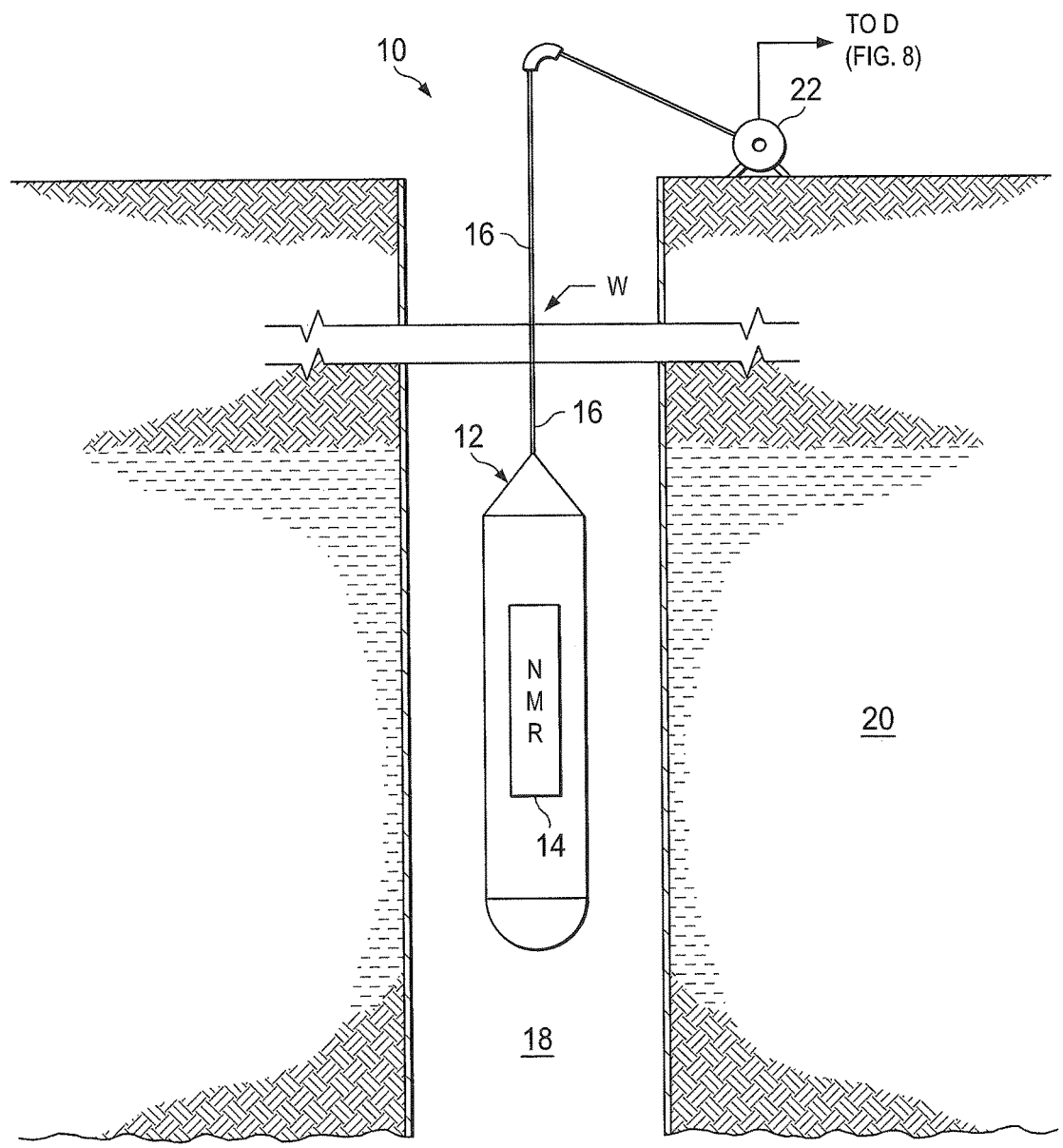
FIG. 1 is a schematic diagram view taken partly in cross-section of a well logging tool for obtaining nuclear magnetic resonance (NMR) measurements at depths of interest in a well in subsurface formations according to the present invention.

In the drawings, a conventional well logging system W is shown in FIG. 1 at a well 10. A sonde 12 containing a nuclear magnetic resonance or NMR well logging system 14 with conventional processing and surface communication instrumentation is lowered by a conductive wireline cable 16 into a well bore 18 to obtain the responses of subsurface formations 20 at depths of interest. In the context of the present invention, the formations of interest are tight gas reservoirs in formations containing methane and other hydrocarbon gases. According to the present invention, tight gas reservoirs include shales, tight siliciclastic sands and tight carbonates.

NMR logging measures the induced magnetization of hydrogen nuclei (protons) contained within the fluid-filled pore space of porous media (reservoir rocks). Low frequency (in a spectrum from about a few hundred kHz to about a few mHz) NMR-logging measurements respond to the presence of mobile hydrogen protons, rather than measuring both the rock matrix and fluid properties of formations. Because the mobile protons primarily occur in pore fluids, nuclear magnetic resonance effectively responds to the volume, composition, viscosity, and distribution of hydrogen containing fluids, which for the purposes of reservoir evaluation are: oil, hydrocarbon gas and water.

Figure 8:
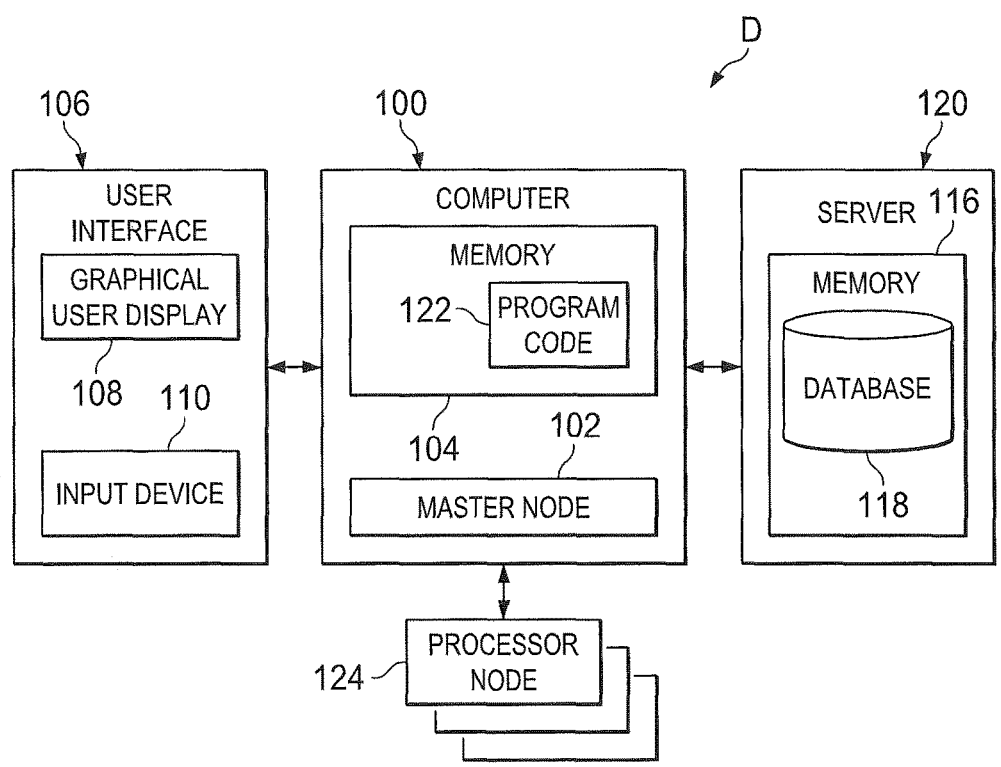
FIG. 8 is a schematic block diagram of a data processing system for measurement of hydrocarbon content of shale gas reservoir according to the present invention.

During the well logging runs, the sonde 12 and cable 16 are suitably supported, by a sheave wheel 22. The NMR well logging measurements obtained by the well logging system 14 are recoded as functions of borehole depth and transferred to the surface over wireline cable 16 to a suitable data memory as input data for a data processing system D (FIG. 8). As will be set forth, the NMR well logging measurements are processed in the data processing system D according to the present invention to determine measures of hydrocarbon content of shale gas reservoir in formations of interest. The processed results from data processing system D are then available for analysis by reservoir engineers or analysts.

Nomenclature

In the following description, symbols are utilized which have the following meanings:

| Symbol | Meaning |
|---|---|
| $\Phi_{well\,log}^{NMR}$ | Total measured fluid |
| $\Phi_{HC}$ | Total hydrocarbon |
| $\Phi_{H_2O}$ | Water content in the rock |
| $\Phi_{cuttings}^{NMR}$ | Fluid content of the cuttings |
| $v_{pm}$ | Measured fluid volume of the drilling mud |
| $W_{pm}$ | Total weight of the drilling mud |
| $V_{pm}$ | Total volume of the drilling mud |
| $X_m^w$ | Fluid content in unit weight of the pure drilling mud |
| $X_m^v$ | Fluid content in unit volume of the pure drilling mud |
| $\alpha$ | Ratio of the short, small $T_2$ peaks to the long, large peaks of the pure drilling mud |
| $v_{pm}^s$ | Volume of short, small $T_2$ peaks of pure drilling mud |
| $v_{pm}^l$ | Volume of long, large $T_2$ peaks of pure drilling mud |
| $v_{c+m}$ | Volume of total measured fluid |
| $v_w$ | Volume of water in drill cuttings |
| $v_m$ | Volume of fluid from drilling mud |
| $v_{c+m}^s$ | Volume of short, small $T_2$ peaks of total fluid |
| $v_{c+m}^l$ | Volume of long, large $T_2$ peaks of total fluid |
| $W_m$ | Weight of drilling mud in total fluid |
| $V_m$ | Volume of drilling mud in total fluid |
| $W_c$ | Weight of water in the cuttings |
| $V_c$ | Volume of water in cuttings |
| $\Phi_{dc}^{NMR}$ | Water in the drill cutting |
| $W_{c+m}$ | Total weight of cuttings and mud |
| $V_{c+m}$ | Total volume of cuttings and mud |

Fluid Content in the Reservoir Condition Measured by NMR Log

Figure 2:
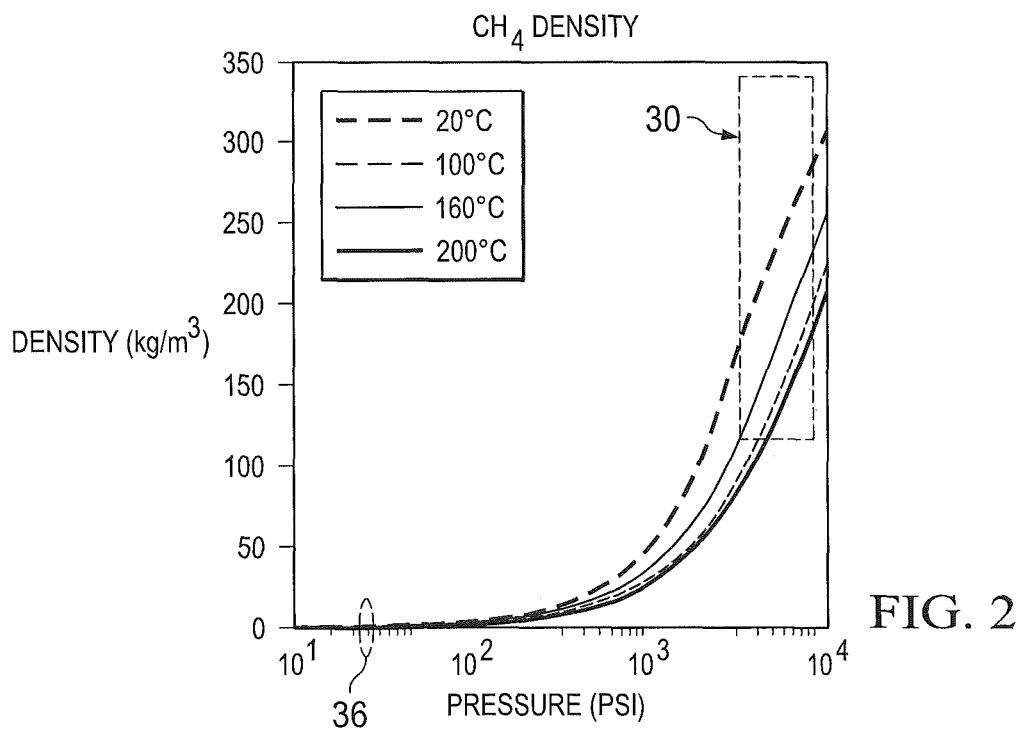
FIG. 2 is a plot of densities of methane as a function of pressure for several example temperatures.

The pore pressure for a typical shale gas reservoir is larger than 4,000 psi. At this pressure, the methane density as a shale gas is more than 100 kg/m$^3$. The real density of hydrocarbon in the pores of shale can be higher than predicted by the bulk state equation. First, the density of adsorbed hydrocarbon on the nanopore surface in kerogen has a density close to liquid at reservoir pressure. Thus, the average hydrocarbon density in the porous system would be higher than in a pure gas state at the given pressure and temperature. If other heavier hydrocarbon compounds are extant in the reservoir and capillary condensation has occurred, then the hydrocarbon density is close to that of liquid, about 500 kg/m$^3$. The density is somewhere within the rectangle 30 of FIG. 2. FIG. 2 is a plot of densities of methane as a function of pressure for several example temperatures.

In the density measures shown in FIG. 2, surface adsorption and possible capillary condensation have been considered. At this density, the hydrocarbon gas can be easily measured by the NMR logging system 14.

Figure 3:
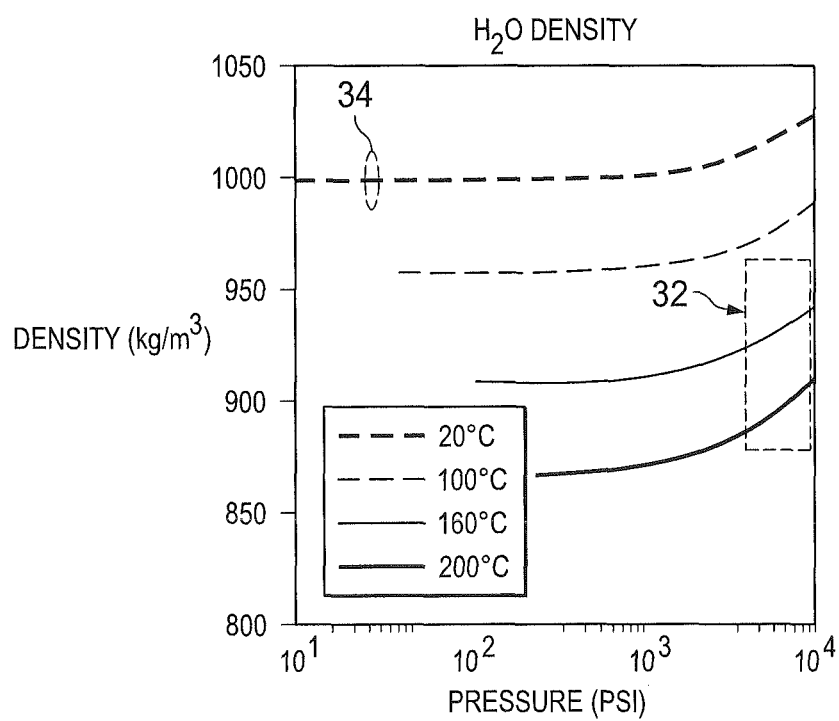
FIG. 3 is a plot of densities of water as a function of pressure for several example temperatures.

At reservoir conditions, the water density is about 10% smaller than the density at surface conditions. FIG. 3 is a plot of densities of water as a function of pressure for several example temperatures. From FIG. 3 it is apparent that temperature has a much greater impact on density of water than pressure. As shown in FIG. 3, water density at reservoir conditions is in a range indicated by a rectangle 32. An ellipse 34 in FIG. 3 illustrates a range of water densities at earth surface conditions. Water presence in a shale formation can thus be easily measured by NMR logging system 14. Therefore, the total measured fluid, $\Phi_{well\ log}^{NMR}$, can be expressed as:

$$\Phi_{well\ log}^{NMR} = \Phi_{HC} + \Phi_{H_2O} \quad (1)$$

in which $\Phi_{HC}$ and $\Phi_{H_2O}$ represent the total hydrocarbon and water content in the rock, respectively. For a sensitive measurement with sufficient accuracy, the NMR logging system 14 should be run slowly through the well bore 18, or, if possible, by using station-stop measurements at desired locations in the well bore 18.

Fluid Content in Drill-Cuttings at the Surface Condition

With the present invention, samples of formation shale in the form of drill-cuttings are obtained from well fluids, which are normally in the form of a drilling mud or OBM. The present invention can also be performed with core samples of the formation shale to the extent that such core samples are available from the formation shales of interest.

When the drill cuttings or rock samples are brought to the earth's surface, the pressure surrounding them is reduced to atmospheric pressure—about 1 atm, with a surface temperature of about 20° C. During this process, the hydrocarbon gas bleeds off to equilibrate with surrounding atmospheric pressure. If not, the large pore pressure of hydrocarbon gas in the shale would fracture the rocks and allow the gas to escape.

At surface pressures and temperatures, the hydrocarbon is in gas state with a density close to zero, as shown somewhere around an ellipse 36 in FIG. 2. At this low density, nuclear magnetic resonance measurement of the shale cuttings is not capable of detecting a signal from the hydrocarbons. In contrast, the water density at surface condition is higher than at the reservoir conditions, as illustrated in FIG. 3 by an ellipse at surface condition as compared to a rectangle indicating example water density at reservoir conditions. However, the water density change does not alter the total water content provided the NMR measurement is done sufficiently quickly after the rocks are surfaced.

The water density increase of the water in shale cuttings as the cuttings are surfaced is most likely achieved by water volume reduction. Void space so formed in the cuttings can fill with hydrocarbon gas from neighboring pores or air, if the cores are exposed to the environment sufficiently long. It is also unlikely that water from external sources could enter into the rock pores, because during surfacing the pressure inside the rock is higher than atmospheric pressure at the earth's surface, and because these tight rocks have permeability in the nD range. For these reasons, it is advantageous to carry out the NMR measurement of the formation rock, whether cuttings or core samples, either at the well-site or within a few hours surfacing to avoid water loss or gain from the environment The densities of methane and water in FIGS. 2 and 3 are calculated using measures from industry sources or field data. The rectangles and ellipses in FIGS. 2 and 3 show approximate values for the reservoir and surface conditions, respectively. For the purposes of the present invention, it is not necessary to obtain or use density measures at reservoir or surface conditions for either water or gas.

An NMR measurement of the fluid within the cuttings $\Phi_{cuttings}^{NMR}$ is then given by:

$$\Phi_{cuttings}^{NMR} = \Phi_{H_2O} \quad (2)$$

Total Hydrocarbon Content for Gas-in-Place Estimation

The subtraction of the NMR well log and the water in drill cuttings then gives the total hydrocarbon content.

$$\Phi_{HC} = \Phi_{well\ log}^{NMR} - \Phi_{cuttings}^{NMR} \quad (3)$$

It should be noted that the water content can also be directly measured from whole cores using whole core NMR and the total hydrocarbon is obtained from Equation (3) by replacing the last term with results of whole core.

NMR Measurement of Water in the Drill-Cuttings in the Presence of Drilling Mud

Physical Principle

The majority of shale gas reservoirs are drilled using drilling mud. In the embodiment herein described, the well bore fluid is thus regarded as drilling mud. However, it should be understood that the methodology of the present invention is also suitable where other types of drilling fluids are the well bore fluid. The surfaced drill-cuttings therefore always contain some well bore fluid, in this embodiment drilling mud, the presence of which contributes to the overall signal resulting from nuclear magnetic resonance measurement. Although it is possible to use fluids containing no hydrogen to wash off the mud from the cuttings before NMR measurement, a direct measurement of the water content of cuttings in the presence of drilling mud is preferable. Thus, the embodiment herein described is in relation to a nuclear magnetic resonance measurement method to measure water content in drill-cuttings in the presence of drilling mud.

Figure 4:
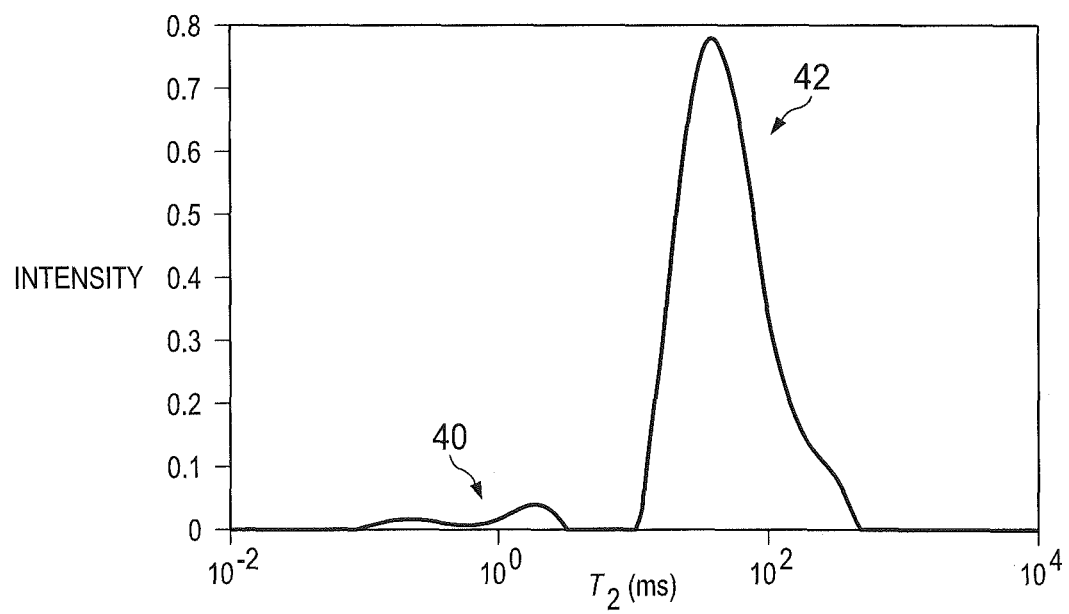
FIG. 4 is a plot of an example nuclear magnetic resonance transverse relaxation spectrum for a drilling mud.
Figure 5:
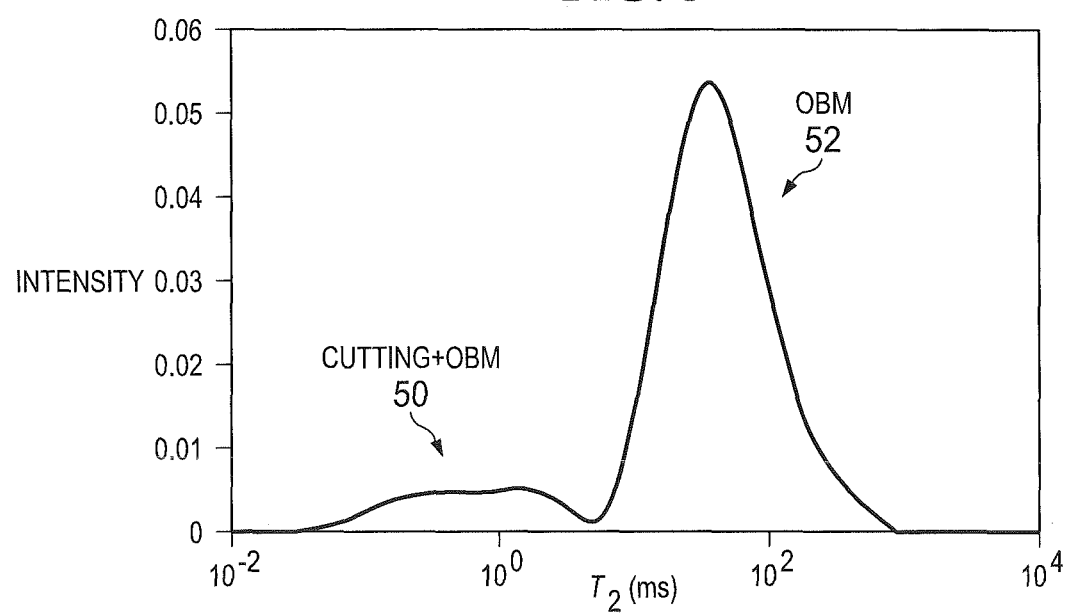
FIG. 5 is a plot of an example nuclear magnetic resonance transverse relaxation spectrum for a sample of shale cuttings and drilling mud.

The nuclear magnetic resonance measurement, according to the present invention, is based on a physical principle that the nuclear magnetic resonance transverse relaxation time $T_2$ of water in shales is short; and in contrast, that the majority of the fluid signal from drilling mud has a long transverse relaxation time $T_2$. Depending on the particles in the drilling mud, fluid signals from the drilling mud, when plotted, form clusters into two regions. FIG. 4 is a plot of an example nuclear magnetic resonance transverse relaxation $T_2$ spectrum for a representative drilling mud with signal clusters 40 and 42. FIG. 5 is a plot of an example nuclear magnetic resonance transverse relaxation spectrum for a sample of shale cuttings and drilling mud, with signal clusters 50 and 52. As can be seen on comparison of FIGS. 4 and 5, the nuclear magnetic resonance transverse relaxation $T_2$ spectrum of water in the shale and the short $T_2$ signals ($T_2$<4.5 ms) of a representative drilling mud generally overlap each other. With the present invention it has been found that the contribution of hydrogen in the drilling mud with cuttings provides a capability to measure hydrocarbon content of shale gas reservoir. The signal cluster of the short $T_2$ signals ($T_2$<4.5 ms) at 50 in FIG. 5 indicates such a hydrogen content. The signal cluster of the short $T_2$ signals ($T_2$<4.5 ms) at 50 in FIG. 5 for drilling mud with cuttings can be seen to differ from the signal cluster 40 of FIG. 4 for the short $T_2$ signals ($T_2$<4.5 ms) of drilling mud.

The previous discussion about hydrogen contribution in drilling mud with cuttings is also based an assumption that a ratio of the amplitude signal clusters between the two signal clusters for the nuclear magnetic resonance transverse relaxation spectrum is the same for both for pure drilling mud (FIG. 4) and for an drilling mud mixed with cuttings (FIG. 5). The method of nuclear magnetic resonance measurement of water in cuttings in the presence of drilling mud according to the present invention is based on the assumptions that water inside the shale cuttings has short nuclear magnetic resonance relaxation time, and that the fluid from drilling mud maintains the same magnetic resonance relaxation time $T_2$ spectrum even in the presence of cuttings.

Formulation of Method

Several parameters can be measured from the NMR $T_2$ of a known amount (weight and volume) of drilling mud: the fluid content in unit weight of the pure mud $X_m^w$ can be measured as:

$$X_m^w = v_{pm}/W_{pm} \tag{4a}$$

Similarly, the fluid content in unit volume of the pure mud $X_m^v$ can be measured as:

$$X_m^v = v_{pm}/V_{pm} \tag{4b}$$

The three measurement relationships $v_{pm}$, $W_{pm}$, and $V_{pm}$ are the fluid volume of the drilling mud, total weight of the drilling mud, and total volume of the drilling mud, respectively.

The ratio a of the short, small $T_2$ peaks to the long, large peaks of the total mud can be expressed as:

$$\alpha = v_{pm}^s/v_{pm}^l \tag{5}$$

Again, it is assumed that when drilling mud is mixed with cuttings, the measured NMR $T_2$ spectrum maintains the same ratio of small $T_2$ peaks to large $T_2$ peaks as pure drilling mud in Equation (5).

For a sample of cuttings with drilling mud, the nuclear magnetic resonance $T_2$ spectrum measures the total fluid: the summation of water in the cuttings and fluid from mud:

$$v_{c+m} = v_w + v_m \tag{6}$$

in which $v_{c+m}$, $v_w$, and $v_m$ are the volumes of total measured fluid, water in the drill-cuttings, and fluid from mud, respectively. The small $T_2$ peak, $v_{c+m}^s$, includes the total water in the cuttings and some mud, the large $T_2$ peak is solely from mud (see FIG. 5). With the mud contribution to the small $T_2$ and the large $T_2$ peaks remaining to be a as in Equation (5), the relation is:

$$v_{c+m}^s = v_w + \alpha v_{c+m}^l \tag{7}$$

in which $v_{c+m}^s$ and $v_{c+m}^l$ are the fluid volume measured from the small $T_2$ and the large $T_2$ regions of the NMR spectrum.

The water volume in the sample is then $$v_w = v_{c+m}^s - \alpha v_{c+m}^l \tag{8}$$

and the fluid volume from mud is $$v_m = v_{c+m} - v_{c+m}^s + \alpha v_{c+m}^l \tag{9}$$

Using Equation (4) and Equation (9), the weight and volume of mud in the cutting sample are:

$$W_m = (v_{c+m} - v_{c+m}^s + \alpha v_{c+m}^l)/X_m^w \tag{10a}$$

$$V_m = (v_{c+m} - v_{c+m}^s + \alpha v_{c+m}^l)/X_m^v \tag{10b}$$

In the lab or in the field, the total weight $W_{c+m}$ and volume $V_{c+m}$ of cutting samples can be easily measured. Using Equation (10), the weight and volume of pure cuttings (including the inherent fluid) are then a simple subtraction of the total by the mud $$W_c = W_{c+m} - (v_{c+m} - v_{c+m}^s + \alpha v_{c+m}^l)/X_m^w \tag{11a}$$

$$V_c = V_{c+m} - (v_{c+m} - v_{c+m}^s + \alpha v_{c+m}^l)/X_m^v \tag{11b}$$

The measured water in the drill cuttings in porosity-unit is $$\Phi_{dc}^{NMR} = \frac{v_w}{V_c} \tag{12}$$

Using Equation (8) and Equation (12), the measured water in the drill cuttings can be expressed as:

$$\Phi_{dc}^{NMR} = \frac{v_{c+m}^s - \alpha v_{c+m}^l}{V_{c+m} - (v_{c+m} - v_{c+m}^s + \alpha v_{c+m}^l)/X_m^v} \tag{13}$$

The measured quantity values on the right of Equation (13) can be measured either from drill-cuttings sample or from a pure mud sample. The water in the cutting $\Phi_{dc}^{NMR}$ is accordingly determined. For the determined water measure for cuttings at the surface, the measure of hydrocarbons $\Phi_{HC}$ present in situ in the formation adjacent to the borehole is then determined during step 72 according to Equation (3) from the well log measurement in situ, $\Phi_{well\ log}^{NMR}$.

Figure 6:
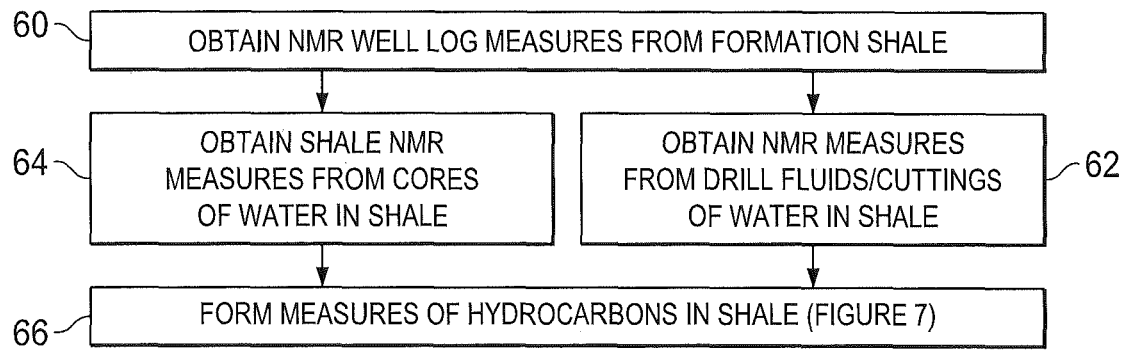
FIG. 6 is a schematic diagram of a process for measurement of hydrocarbon content of shale gas reservoir according to the present invention.

In the drawings, a flowchart F (FIG. 6) indicates a basic computer processing sequence of the present invention for determination of hydrocarbon content of a shale gas reservoir according to the present invention. As indicated at step 60, nuclear magnetic resonance well log measures are obtained in situ from a shale formation with the logging system W as shown in FIG. 1. FIG. 3 is an example plot of the type of data so obtained. During step 62, in situations where cores samples are not available for shale formation of interest, nuclear magnetic resonance measures are obtained from surface evaluation of the drilling mud cuttings regarding the presence of water in the shale. In situations where core samples of the formation of interest are available, as an alternative step 64 is performed to obtain nuclear magnetic resonance measures from surface testing of the water present in the core samples. As indicated at step 66, after either of steps 62 or 64, measures are determined during step 66 by processing as illustrated schematically in FIG. 7 to determine measures of hydrocarbons in the formation shale.

Figure 7:
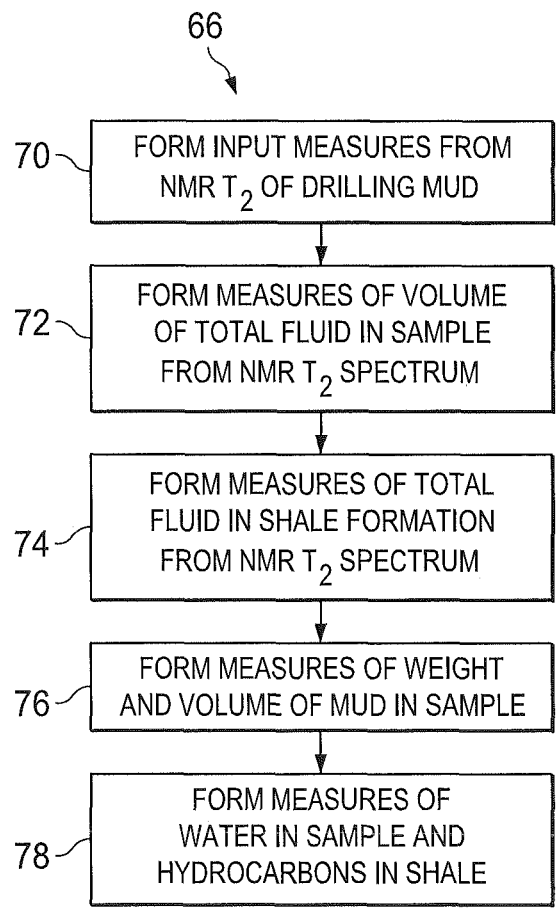
FIG. 7 is a functional block diagram of a set of data processing steps performed in a data processing system for measurement of hydrocarbon content of shale gas reservoir according to the present invention.

As shown in FIG. 7, computer implemented processing, according to the present invention, to determine measures of hydrocarbons present in formation shale begins with step 70, where input measures are formed of the drilling mud based on nuclear magnetic resonance relaxation $T_2$ spectra. During step 72, measures are formed from the $T_2$ spectra of the volume of total fluid in the samples at the surface.

In step 74, measures of the total fluid in the shale formation are obtained based on $T_2$ spectra. Step 76 involves obtaining measures of the weight and volume of the mud in the samples. Subsequently, in step 78, a measure of the water $\Phi_{dc}^{NMR}$ in the samples is determined based on the relationship expressed in Equation (13) and the physical measures obtained from the formations, drill cuttings and drilling mud. The measure of hydrocarbons $\Phi_{HC}$ in situ is then determined according to the relation expressed in Equation (3) between total measured fluid in situ, obtained by the well logging system W, and water content of the drill cuttings, measured at the surface.

As illustrated in FIG. 8, the data processing system D includes a computer 100 having a master node processor 102 and memory 104 coupled to the processor 102 to store operating instructions, control information and database records therein. The data processing system D is preferably a multicore processor with nodes such as those from Intel Corporation or Advanced Micro Devices (AMD), or an HPC Linux cluster computer. The data processing system D may also be a mainframe computer of any conventional type with suitable processing capacity such as those available from International Business Machines (IBM) of Armonk, N.Y. or other source. The data processing system D may also be a computer of any conventional type of suitable processing capacity, such as a personal computer, laptop computer, or any other suitable processing apparatus. It should thus be understood that a number of commercially available data processing systems and types of computers may be used for this purpose.

The computer 100 is accessible to operators or users through user interface 106 and is available for displaying output data or records of processing results obtained according to the present invention with an output graphic user display 108. The output display 108 includes components such as a printer and an output display screen capable of providing printed output information or visible displays in the form of graphs, data sheets, graphical images, data plots and the like as output records or images.

The user interface 106 of the computer 100 also includes a suitable user input device or input/output control unit 110 to provide the user access to control or access information and database records and operate the computer 100. The data processing system D further includes a database 112 of data stored in computer memory, which may be internal memory 104, or an external, networked, or non-networked memory as indicated at 116 in an associated database 118 in a server 120.

The data processing system D includes program code 122 stored in non-transitory memory 104 of the computer 100. The program code 122 according to the present invention is in the form of computer operable instructions causing the data processor 102 to form measures of hydrocarbon content of a shale gas reservoir according to the present invention in the manner that has been set forth.

It should be noted that the program code 122 may be in the form of microcodes, programs, routines, or symbolic computer operable languages that provide a specific set of ordered operations that control the functioning of the data processing system D and direct its operation. The instructions of the program code 122 may be stored in the memory 104 of the data processing system D, or on a computer diskette, magnetic tape, conventional hard disk drive, electronic read-only memory, optical storage device, or other appropriate data storage device having a computer usable non-transitory medium stored thereon. The program code 122 may also be contained on a data storage device, such as a server 120, as a non-transitory computer readable medium.

The data processing system D may be comprised of a single CPU, or a computer cluster as shown in FIG. 4, including computer memory and other hardware that makes it possible to manipulate data and obtain output data from input data. A cluster is a collection of computers, referred to as nodes, connected via a network. Usually a cluster has one or two head nodes, or master nodes 102, that are used to synchronize the activities of the other nodes, referred to as processing nodes 124. The processing nodes 124 each execute the same computer program and work independently on different segments of the grid which represents the reservoir.

From the preceding, it can be seen that the present invention determines measures of the hydrocarbon content in a shale gas formation or reservoir. Nuclear magnetic resonance well logs obtain measures of the total fluid, including both water and hydrocarbon, in the shale of the reservoir. Nuclear magnetic resonance measurement of shale drill cuttings obtained at the surface from the same well provide measures of total water content of the shale.

At the surface, pressure on the drill cuttings becomes that of atmospheric pressure, and hydrocarbon gas contained in the shale cuttings bleeds off. The remaining fluid within the shale cuttings is then only water, which can be measured using nuclear magnetic resonance techniques. Compensation for the effect of drilling fluids (drilling mud) on the nuclear magnetic resonance measures from the drill cuttings is also performed. The hydrocarbon gas content of the formation shale is determined from the difference between formation nuclear magnetic resonance well log readings and nuclear magnetic resonance measurements from drill cuttings.

The present invention also provides a method for determining hydrocarbon content of formation shale based on the measures of water content obtained from drill cuttings. This does not require additional operation cost, such as core sampling. The present invention can be performed continuously to measure samples along a well while well operations are in progress, rather than a separate test based on core samples at some earlier time. The present eliminates the complicated sample preparation and preservation required to maintain fluid content in the core for accurate results. Further, the present invention can be done at a well-site.

The present invention does not require knowledge of where and how hydrocarbon is stored in the shale pores. The present invention thus avoids the inherent problems described in detail above regarding current well-log based methods and/or core-measurement based methods.

The invention has been sufficiently described so that a person with average knowledge in the matter may reproduce and obtain the results mentioned in the invention herein Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

What is claimed is:

1. A method of determining hydrocarbon gas content of a pressurized subsurface tight gas formation at a depth of interest in the earth adjacent a well, the well having therein well fluids comprising drilling mud and formation drill cuttings containing drilling mud, the hydrocarbon gas content being determined from nuclear magnetic resonance well logging responses obtained by a nuclear magnetic resonance well logging system in the well and nuclear magnetic resonance of the well fluids by performing the steps of:

(a) lowering a sonde containing the nuclear magnetic resonance well logging system by a wireline cable into the well to obtain without measuring porosity the nuclear magnetic resonance well logging responses of the pressurized subsurface tight gas formation in situ at the depth of interest;

(b) obtaining nuclear magnetic resonance relaxation time spectra in situ from the obtained nuclear magnetic resonance responses of the pressurized subsurface tight gas formation, the obtained relaxation time spectra indicating water and hydrocarbon fluid content in the pressurized subsurface tight gas formation;

(c) forming a measure of the fluid content in the pressurized subsurface tight gas formation based on the obtained nuclear magnetic resonance relaxation time spectra from the nuclear magnetic responses of the pressurized subsurface tight gas formation;

(d) obtaining a sample of pure drilling mud for the well at the earth surface;

(e) obtaining nuclear magnetic resonance relaxation time spectra from nuclear magnetic resonance measurements of the obtained sample of pure drilling mud for the well, the obtained nuclear magnetic resonance relaxation time spectra indicating water content of the pure drilling mud for the well;

(f) obtaining a sample of the well fluid brought to the earth surface containing the pure drilling mud and formation drill cuttings from the well;

(g) obtaining nuclear magnetic resonance relaxation time spectra from nuclear magnetic resonance measurements of the obtained sample of the well fluid, the obtained relaxation time spectra indicating water content of the obtained sample of the well fluid;

(h) forming a measure of water content in the obtained formation drill cuttings based on the obtained nuclear magnetic resonance relaxation time spectra of the obtained sample of the well fluid; and (i) determining the hydrocarbon gas content of the pressurized subsurface tight gas formation from the formed measure of the water and hydrocarbon fluid content in situ of the pressurized subsurface tight gas formation and the formed measure of the water content at the earth surface in the obtained formation drill cuttings.

2. The method of claim 1, wherein the pressurized subsurface tight gas formation is selected from the group consisting of tight gas shales, tight siliciclastic gas sands, and tight gas carbonates.

3. The method of claim 1, wherein the measure of the water content in the formation drill cuttings comprises a measure of water content as a function of volume.

4. The method of claim 1, further including the step of: compensating for the presence of drilling mud in the obtained formation drill cuttings during the step of obtaining a measure of the water content in the obtained formation drill cuttings.

5. The method of claim 1, wherein the step of determining the hydrocarbon gas content of the pressurized subsurface tight gas formation from the formed measure of the water and hydrocarbon fluid content in situ of the pressurized subsurface tight gas formation and the formed measure of the water content at the earth surface in the obtained formation drill cuttings is performed by computer processing and comprises computer implemented steps of:

(a) forming measures of the volume of total fluids present in the obtained formation drill cuttings based on nuclear magnetic resonance relaxation time spectra obtained from nuclear magnetic resonance measures of the obtained sample of the well fluid;

(b) forming measures of the volume of water present in the obtained formation drill cuttings based on nuclear magnetic resonance relaxation time spectra obtained from nuclear magnetic resonance measures of the obtained sample of the well fluid;

(c) forming measures of the weight and volume of the obtained sample of the well fluid; and (d) forming a measure of water content in the obtained sample of the well fluid.

* * * * *